United States Patent [19]
Lawlor

[11] Patent Number: 6,051,412
[45] Date of Patent: Apr. 18, 2000

[54] GLYCYL TRNA SYNTHETASE FROM *STREPTOCOCCUS PNEUMONIAE*

[75] Inventor: Elizabeth Jane Lawlor, Malvern, Pa.

[73] Assignees: SmithKline Beecham Corporation, Philadelphia, Pa.; SmithKline Beecham p.l.c., United Kingdom

[21] Appl. No.: 09/012,952

[22] Filed: Jan. 23, 1998

Related U.S. Application Data

[62] Division of application No. 08/844,085, Apr. 18, 1997, Pat. No. 5,756,330.

[30] Foreign Application Priority Data

Apr. 18, 1996 [GB] United Kingdom ............ 9608002

[51] Int. Cl.[7] .............................. C12N 9/00; C12N 15/00; C12Q 1/68; C07H 21/04
[52] U.S. Cl. .............................. 435/183; 435/6; 435/440; 530/387.1; 536/23.2
[58] Field of Search ................. 435/6, 186, 440; 530/387.1; 536/23.2

[56] References Cited

PUBLICATIONS

Webster et al., "Primary Structures of Both Subunits of *Escherichia coli* Glycyl–tRNA Synthetase," *Journal of Biological Chemistry*, 258(17) p. 10637–10641 (1983).

Fleischmann et al., "Whole–Genome Random Sequencing and Assembly of Haemophilius influenzae Rd.," *Science*, 269 p. 496–512 (1995).

R. Calendar et al., "Purification and Physical Characterization of Tyrosyl Ribonucleic Acid Synthetases from *Escerichia coli* and *Bacillus subtilis*", *Biochemistry*, 5(5) p. 1681–1690.

J. Hughes et al., "How Does *Pseudomonas Fluorescens*, the Producing Organism of the Antibiotic Pseudomonic Acid A, Avoid Suicide?", *FEBS Letters*, 122(2) p. 322–324 (1980).

Niyomporn et al., "Biosynthesis of the Peptidogylcan of Bacterial Cell Walls", *J. Biol. Chem.*, 243(4) p. 773–778 (1968).

Lindler, et al., "Molecular Cloning and Characterization of a Streptococcus DNase Necessary for Repair of DNA Damage Induced by UV Light and Methyl Methanesulfonate", *Journal of Bacteriology*, vol. 169, No. 7: pp. 3199–3208, 1987.

*Primary Examiner*—Lisa J. Hobbs
*Attorney, Agent, or Firm*—Edward R. Gimmi; William T. King; Thomas S. Deibert

[57] ABSTRACT

The invention provides glyS (beta) and glyS (alpha) polypeptides and DNA (RNA) encoding glyS (beta) and glyS (alpha) polypetides and methods for producing such polypeptides by recombinant techniques. Also provided are methods for utilizing glyS (beta) and glyS (alpha) polypeptides to screen for antibacterial compounds.

29 Claims, No Drawings

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 2037 base pairs
      (B) TYPE: nucleic acid (C) STRANDEDNESS: single
        (D) TOPOLOGY: linear (ii) MOLECULE TYPE: Genomic DNA (xi) SEQUENCE DESCRIPTION: SEQ ID NO:1:

| | | | | | |
|---|---|---|---|---|---|
| ATGACAAAAA | ACTTATTAGT | AGAACTCGGT | CTTGAAGAAT | TACCAGCCTA | TGTTGTCACA | 60 |
| CCAAGTGAAA | AACAACTAGG | CGAAAAAATG | GCAGCCTTCC | TCAAGGAAAA | CCGCCTGTCT | 120 |
| TTTGAAGCCA | TTCAAACCTT | CTCAACACCA | CGTCGTTTGG | CTGTTCGTGT | GACTGGTTTA | 180 |
| TCAGACAAAC | AGTCTGATTT | GACAGAAGAT | TTCAAGGGAC | CAGCAAAGAA | AATTGCCTTG | 240 |
| GATAGTGATG | GAAACTTCAC | CAAAGCAGCT | CAAGGATTTG | TCCGTGGAAA | AGGCTTGACT | 300 |
| GTTGAAGATA | TCGAATTCCG | TGAAATCAAG | GGTGAAGAAT | ATGTCTATGT | CACTAAGGAA | 360 |
| GAAGTTGGTC | AAGCAGTTGA | AGCCATTGTT | CCTGGTGTTG | TAGATGTCTT | GAAGTCATTG | 420 |
| ACTTTCCCTG | TCAGCATGCA | CTGGGCTGGA | AACAGCTTTG | AATACATCCG | CCCTGTTCAC | 480 |
| ACTTTAACTG | TTCTCTTGGA | TGAGCAAGAG | TTTGACTTGG | ATTTCCTTGA | TATCAAGGGA | 540 |
| GGTCGTGTGA | GCCGTGGCCA | TCGTTTTCTT | GGGAAAGAAA | CCAAAATTCA | GTCAGCATTG | 600 |
| AGCTATGAAG | AAGACCTTCG | TAAGCAGTTT | GTAATCGCAG | ATCCATGTGA | ACGTGAGCAA | 660 |
| ATGATTGTTG | ACCAAATCAA | GAAAATTGAG | GCAAACATG | GTGTACGTAT | CGAAATTGAT | 720 |
| GCGGATTTGC | TGAATGAAGT | CTTGAATTTG | GTTGAATACC | CAACTGCCTT | CATGGGAAGT | 780 |
| TTTGATGCTA | ATACCTTGA | AGTTCCAGAA | GAAGTCTTGG | TAACTTCTAT | GAAGGAACAC | 840 |
| CAGCGTTACT | TTGTTGTTCG | TGATCAAGAT | GGAAAACTCT | TGCCAAACTT | CATTTCTGTT | 900 |
| CGTAACGGAA | ACGCAGAGCG | TTTGAAAAAT | GTCATCAAAG | GAAATGAAAA | AGTCTTGGTA | 960 |
| GCCCGCTTGG | AAGACGGAGA | ATTCTTCTGG | CGTGAAGACC | AAAAATTGGT | GATTTCAGAT | 1020 |
| CTTGTTGAAA | AATTAAACAA | TGTCACCTTC | CATGAGAAGA | TTGGTTCCCT | TCGTGAACAC | 1080 |
| ATGATTCGTA | CGGGTCAAAT | CACTGTACTT | TTGGCAGAAA | AAGCTGGTTT | GTCAGTGGAT | 1140 |
| GAAACAGTTG | ACCTTGCTCG | TGCAGCAGCC | ATTTACAAGT | TTGACTTGTT | GACAGGTATG | 1200 |
| GTTGGTGAAT | TTGACGAACT | CCAAGGAATT | ATGGGTGAAA | AATACACCCT | TCTTGCTGGT | 1260 |
| GAAACTCCAG | CGGTGGCAGC | TGCTATTCGT | GAACACTACA | TGCCTACATC | AGCTGAAGGA | 1320 |
| GAACTTCCAG | AGAGCAAGGT | CGGTGCAGTT | CTAGCCATTG | CAGACAAATT | GGATACGATT | 1380 |
| TTGAGTTTCT | TCTCAGTAGG | ATTGATTCCA | TCAGGTTCTA | ATGACCCTTA | TGCCCTTCGT | 1440 |
| CGTGCAACTC | AAGGTGTGGT | TCGTATCTTG | GATGCCTTTG | GTTGGCACAT | TGCTATGGAT | 1500 |
| GAGCTGATTG | ATAGCCTTTA | TGCATTGAAA | TTTGACAGTT | TGACTTATGA | AAATAAAGCA | 1560 |
| GAGGTTATGG | ACTTTATCAA | GGCTCGTGTT | GATAAGATGA | TGGGCTCTAC | TCCAAAAGAT | 1620 |
| ATCAAGGAAG | CAGTTCTTGC | AGGTTCAAAC | TTTGTTGTGG | CAGATATGTT | GGAAGCAGCA | 1680 |
| AGTGCTCTCG | TAGAAGTAAG | CAAGGAAGAA | GATTTTAAAC | CATCTGTTGA | ATCACTTTCT | 1740 |
| CGTGCCTTTA | ACCTGGCTGA | GAAGGCAGAA | GGGGTTGCTA | CAGTTGATTC | AGCACTATTT | 1800 |
| GAGAATGACC | AAGAAAAAGC | TTTGGCAGAA | GCAGTAGAAA | CACTCGTTTT | ATCAGGACCT | 1860 |
| GCAAGTCAGC | AATTGAAACA | ACTCTTTGCG | CTTAGCCCAG | TCATTGATGC | TTTCTTTGAA | 1920 |
| AATACTATGG | TAATGGCTGA | AGATCAGGCT | GTCCGTCAAA | ATCGTTTGGC | AATCTTGTCA | 1980 |
| CAACTAACCA | AGAAAGCAGC | TAAGTTTGCT | TGTTTTAACC | AAATTAACAC | TAAATAA | 2037 |

-continued (2) INFORMATION FOR SEQ ID NO:2:

(i) SEQUENCE CHARACTERISTICS:
        (A) LENGTH: 678 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Thr Lys Asn Leu Leu Val Glu Leu Gly Leu Glu Glu Leu Pro Ala
  1               5                  10                  15

Tyr Val Val Thr Pro Ser Glu Lys Gln Leu Gly Glu Lys Met Ala Ala
             20                  25                  30

Phe Leu Lys Glu Asn Arg Leu Ser Phe Glu Ala Ile Gln Thr Phe Ser
         35                  40                  45

Thr Pro Arg Arg Leu Ala Val Arg Val Thr Gly Leu Ser Asp Lys Gln
     50                  55                  60

Ser Asp Leu Thr Glu Asp Phe Lys Gly Pro Ala Lys Lys Ile Ala Leu
 65                  70                  75                  80

Asp Ser Asp Gly Asn Phe Thr Lys Ala Ala Gln Gly Phe Val Arg Gly
                 85                  90                  95

Lys Gly Leu Thr Val Glu Asp Ile Glu Phe Arg Glu Ile Lys Gly Glu
            100                 105                 110

Glu Tyr Val Tyr Val Thr Lys Glu Glu Val Gly Gln Ala Val Glu Ala
        115                 120                 125

Ile Val Pro Gly Val Val Asp Val Leu Lys Ser Leu Thr Phe Pro Val
    130                 135                 140

Ser Met His Trp Ala Gly Asn Ser Phe Glu Tyr Ile Arg Pro Val His
145                 150                 155                 160

Thr Leu Thr Val Leu Leu Asp Glu Gln Glu Phe Asp Leu Asp Phe Leu
                165                 170                 175

Asp Ile Lys Gly Gly Arg Val Ser Arg Gly His Arg Phe Leu Gly Lys
            180                 185                 190

Glu Thr Lys Ile Gln Ser Ala Leu Ser Tyr Glu Glu Asp Leu Arg Lys
        195                 200                 205

Gln Phe Val Ile Ala Asp Pro Cys Glu Arg Glu Gln Met Ile Val Asp
    210                 215                 220

Gln Ile Lys Lys Ile Glu Ala Lys His Gly Val Arg Ile Glu Ile Asp
225                 230                 235                 240

Ala Asp Leu Leu Asn Glu Val Leu Asn Leu Val Glu Tyr Pro Thr Ala
                245                 250                 255

Phe Met Gly Ser Phe Asp Ala Lys Tyr Leu Glu Val Pro Glu Glu Val
            260                 265                 270

Leu Val Thr Ser Met Lys Glu His Gln Arg Tyr Phe Val Val Arg Asp
        275                 280                 285

Gln Asp Gly Lys Leu Leu Pro Asn Phe Ile Ser Val Arg Asn Gly Asn
    290                 295                 300

Ala Glu Arg Leu Lys Asn Val Ile Lys Gly Asn Glu Lys Val Leu Val
305                 310                 315                 320

Ala Arg Leu Glu Asp Gly Glu Phe Phe Trp Arg Glu Asp Gln Lys Leu
                325                 330                 335

Val Ile Ser Asp Leu Val Glu Lys Leu Asn Asn Val Thr Phe His Glu
            340                 345                 350
```

```
Lys Ile Gly Ser Leu Arg Glu His Met Ile Arg Thr Gly Gln Ile Thr
            355                 360                 365
Val Leu Leu Ala Glu Lys Ala Gly Leu Ser Val Asp Glu Thr Val Asp
        370                 375                 380
Leu Ala Arg Ala Ala Ala Ile Tyr Lys Phe Asp Leu Leu Thr Gly Met
385                 390                 395                 400
Val Gly Glu Phe Asp Glu Leu Gln Gly Ile Met Gly Glu Lys Tyr Thr
                405                 410                 415
Leu Leu Ala Gly Glu Thr Pro Ala Val Ala Ala Ile Arg Glu His
            420                 425                 430
Tyr Met Pro Thr Ser Ala Glu Gly Glu Leu Pro Glu Ser Lys Val Gly
        435                 440                 445
Ala Val Leu Ala Ile Ala Asp Lys Leu Asp Thr Ile Leu Ser Phe Phe
450                 455                 460
Ser Val Gly Leu Ile Pro Ser Gly Ser Asn Asp Pro Tyr Ala Leu Arg
465                 470                 475                 480
Arg Ala Thr Gln Gly Val Val Arg Ile Leu Asp Ala Phe Gly Trp His
                485                 490                 495
Ile Ala Met Asp Glu Leu Ile Asp Ser Leu Tyr Ala Leu Lys Phe Asp
            500                 505                 510
Ser Leu Thr Tyr Glu Asn Lys Ala Glu Val Met Asp Phe Ile Lys Ala
        515                 520                 525
Arg Val Asp Lys Met Met Gly Ser Thr Pro Lys Asp Ile Lys Glu Ala
    530                 535                 540
Val Leu Ala Gly Ser Asn Phe Val Val Ala Asp Met Leu Glu Ala Ala
545                 550                 555                 560
Ser Ala Leu Val Glu Val Ser Lys Glu Glu Asp Phe Lys Pro Ser Val
                565                 570                 575
Glu Ser Leu Ser Arg Ala Phe Asn Leu Ala Glu Lys Ala Glu Gly Val
            580                 585                 590
Ala Thr Val Asp Ser Ala Leu Phe Glu Asn Asp Gln Glu Lys Ala Leu
        595                 600                 605
Ala Glu Ala Val Glu Thr Leu Val Leu Ser Gly Pro Ala Ser Gln Gln
    610                 615                 620
Leu Lys Gln Leu Phe Ala Leu Ser Pro Val Ile Asp Ala Phe Phe Glu
625                 630                 635                 640
Asn Thr Met Val Met Ala Glu Asp Gln Ala Val Arg Gln Asn Arg Leu
                645                 650                 655
Ala Ile Leu Ser Gln Leu Thr Lys Lys Ala Ala Lys Phe Ala Cys Phe
            660                 665                 670
Asn Gln Ile Asn Thr Lys
        675

(2) INFORMATION FOR SEQ ID NO:3:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:3:

CATCGTTTCT TGGGGAAAGA AACCAAAATT CAGTCAGCAT TGAGCTATGA AGAAGACCTT      60

CGTAAGCAGT TTGTAATCGC ANATCCATGT GAACGTGAGC AAATGATTGT TGACCAAATC     120
```

```
AAGAAAAATTG AGGCAAAACA TGGTGTACGT ATCGAAATTG ATGCGGATTT GCTGAATGAA      180

GTCTTGAATT TGGTTGAATA CCCNACTGCC TTCATGGGAA GTTTTGATGC TAAATNCCTT      240

GAAGTTCCAG AAGAAGTCTT GGTAACTTCT ATGAAGGAAC ACCAGCGTTA CTTTGTTGTT      300

CGTGATCAAG ATGGAAAACT CTTGCCAAAC TTCATTTCTG TTCGTAACGG AAACGCAGAG      360

CGTTTGAAAA ATGTCTTCAA AGGAAATGAA                                      390

(2) INFORMATION FOR SEQ ID NO:4:

(i) SEQUENCE CHARACTERISTICS:
         (A) LENGTH: 130 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:4:

His Arg Phe Leu Gly Lys Glu Thr Lys Ile Gln Ser Ala Leu Ser Tyr
 1               5                  10                  15

Glu Glu Asp Leu Arg Lys Gln Phe Val Ile Ala Xaa Pro Cys Glu Arg
            20                  25                  30

Glu Gln Met Ile Val Asp Gln Ile Lys Lys Ile Glu Ala Lys His Gly
        35                  40                  45

Val Arg Ile Glu Ile Asp Ala Asp Leu Leu Asn Glu Val Leu Asn Leu
 50                  55                  60

Val Glu Tyr Pro Thr Ala Phe Met Gly Ser Phe Asp Ala Lys Xaa Leu
 65                  70                  75                  80

Glu Val Pro Glu Glu Val Leu Val Thr Ser Met Lys Glu His Gln Arg
                85                  90                  95

Tyr Phe Val Val Arg Asp Gln Asp Gly Lys Leu Leu Pro Asn Phe Ile
            100                 105                 110

Ser Val Arg Asn Gly Asn Ala Glu Arg Leu Lys Asn Val Phe Lys Gly
        115                 120                 125

Asn Glu
    130

(2) INFORMATION FOR SEQ ID NO:5:

(i) SEQUENCE CHARACTERISTICS:
         (A) LENGTH: 918 base pairs
         (B) TYPE: nucleic acid
         (C) STRANDEDNESS: single
         (D) TOPOLOGY: linear (ii) MOLECULE TYPE: Genomic DNA (xi) SEQUENCE DESCRIPTION: SEQ ID NO:5:

ATGTCTAAGA AATTAACATT TCAAGAAATT ATTTTGACTT TGCAACAATT TTGGAATGAC       60

CAAGGTTGTA TGCTTATGCA GGCTTATGAT AATGAAAAAG GTGCGGGAAC AATGAGTCCT      120

TACACTTTCC TTCGTGCTAT CGGACCTGAG CCATGGAATG CAGCTTATGT AGAGCCATCA      180

CGTCGTCCTG CTGACGGTCG TTATGGGGAA AACCCTAACC GTCTCTACCA ACACCACCAA      240

TTCCAGGTGG TCATGAAGCC TTCTCCATCA AATATCCAAG AACTTTACCT TGAGTCTTTG      300

GAAAAATTGG GAATCAATCC TTTGGAGCAC GATATTCGTT TTGTTGAGGA CAACTGGGAA      360

AACCCATCAA CTGGTTCAGC TGGTCTTGGT TGGGAAGTTT GGCTTGACGG AATGGAAATC      420

ACTCAGTTCA CTTATTTCCA ACAAGTCGGT GGATTGGCAA CTGGCCCTGT GACTGCGGAA      480
```

```
GTTACCTATG GTTTGGAGCG CTTGGCTTCT TACATTCAAG AAGTAGACTC TGTCTATGAT        540

ATCGAGTGGG CTGATGGTGT AAAATACGGA GAAATCTTTA TCCAGCCTGA GTATGAGCAC        600

TCAAAATATT CATTTGAAAT TTCGAACCAA GAAATGTTGC TTGAAAACTT TGATAAGTTT        660

GAAAAGAAG CTGGTCGTGC ATTAAAAGAA GGCTTGGTAC ACCCTGCCTA TGACTATGTT         720

CTCAAATGTT CACATACCTT TAATCTGCTT GACGCGCGTG GTGCCGTATC TGTAACAGAG        780

CGTGCAGGCT ATATCGCTCG TATCCGTAAC TTGGCCCGTG TTGTAGCCAA AACCTTTGTT        840

GCAGAACGCA AACGCCTAGG TTACCCACTT TTGGATGAAG AAACACGAGT TAAACTTTTA        900

GCAGAAGACG CAGAATAG                                                     918
```

(2) INFORMATION FOR SEQ ID NO:6:

(i) SEQUENCE CHARACTERISTICS:
        (A) LENGTH: 305 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Ser Lys Lys Leu Thr Phe Gln Glu Ile Ile Leu Thr Leu Gln Gln
 1               5                  10                  15

Phe Trp Asn Asp Gln Gly Cys Met Leu Met Gln Ala Tyr Asp Asn Glu
            20                  25                  30

Lys Gly Ala Gly Thr Met Ser Pro Tyr Thr Phe Leu Arg Ala Ile Gly
        35                  40                  45

Pro Glu Pro Trp Asn Ala Ala Tyr Val Glu Pro Ser Arg Arg Pro Ala
    50                  55                  60

Asp Gly Arg Tyr Gly Glu Asn Pro Asn Arg Leu Tyr Gln His His Gln
65                  70                  75                  80

Phe Gln Val Val Met Lys Pro Ser Pro Ser Asn Ile Gln Glu Leu Tyr
                85                  90                  95

Leu Glu Ser Leu Glu Lys Leu Gly Ile Asn Pro Leu Glu His Asp Ile
            100                 105                 110

Arg Phe Val Glu Asp Asn Trp Glu Asn Pro Ser Thr Gly Ser Ala Gly
        115                 120                 125

Leu Gly Trp Glu Val Trp Leu Asp Gly Met Glu Ile Thr Gln Phe Thr
    130                 135                 140

Tyr Phe Gln Gln Val Gly Gly Leu Ala Thr Gly Pro Val Thr Ala Glu
145                 150                 155                 160

Val Thr Tyr Gly Leu Glu Arg Leu Ala Ser Tyr Ile Gln Glu Val Asp
                165                 170                 175

Ser Val Tyr Asp Ile Glu Trp Ala Asp Gly Val Lys Tyr Gly Glu Ile
            180                 185                 190

Phe Ile Gln Pro Glu Tyr Glu His Ser Lys Tyr Ser Phe Glu Ile Ser
        195                 200                 205

Asn Gln Glu Met Leu Leu Glu Asn Phe Asp Lys Phe Glu Lys Glu Ala
    210                 215                 220

Gly Arg Ala Leu Lys Glu Gly Leu Val His Pro Ala Tyr Asp Tyr Val
225                 230                 235                 240

Leu Lys Cys Ser His Thr Phe Asn Leu Leu Asp Ala Arg Gly Ala Val
                245                 250                 255
```

```
Ser Val Thr Glu Arg Ala Gly Tyr Ile Ala Arg Ile Arg Asn Leu Ala
            260                 265                 270

Arg Val Val Ala Lys Thr Phe Val Ala Glu Arg Lys Arg Leu Gly Tyr
            275                 280                 285

Pro Leu Leu Asp Glu Glu Thr Arg Val Lys Leu Leu Ala Glu Asp Ala
            290                 295                 300

Glu
305

(2) INFORMATION FOR SEQ ID NO:7:

(i) SEQUENCE CHARACTERISTICS:
        (A) LENGTH: 201 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:7:

GGTCTTGGTT GGGAAGTTTG GCTTGACGGA ATGGAAATCA CTCAGTTCAC TTATTTCCAA      60

CAAGTCGGTG GATTGGCAAC TGGCCCTGTG ACTGCGGAAG TTACCTATGG TTTGGAGCGC     120

TTGGCTTCTT ACATTCAAGA AGTAGACTCT GTCTATGATA TCGAGTGGGC TGATGGTGTA     180

AAATACGGAG AAATCTTTAT C                                               201

(2) INFORMATION FOR SEQ ID NO:8:

(i) SEQUENCE CHARACTERISTICS:
        (A) LENGTH: 67 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Gly Leu Gly Trp Glu Val Trp Leu Asp Gly Met Glu Ile Thr Gln Phe
 1               5                  10                  15

Thr Tyr Phe Gln Gln Val Gly Gly Leu Ala Thr Gly Pro Val Thr Ala
            20                  25                  30

Glu Val Thr Tyr Gly Leu Glu Arg Leu Ala Ser Tyr Ile Gln Glu Val
            35                  40                  45

Asp Ser Val Tyr Asp Ile Glu Trp Ala Asp Gly Val Lys Tyr Gly Glu
        50                  55                  60

Ile Phe Ile
65

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:9:

ATGACAAAAA ACTTATTAGT AGAA                                             24
```

-continued (2) INFORMATION FOR SEQ ID NO:10:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: Genomic DNA (xi) SEQUENCE DESCRIPTION: SEQ ID NO:10:

TTATTTAAGT GTTAATTTGG TTAA                                                24

(2) INFORMATION FOR SEQ ID NO:11:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: Genomic DNA (xi) SEQUENCE DESCRIPTION: SEQ ID NO:11:

ATGTCTAAGA AATTAACATT TCAA                                                24

(2) INFORMATION FOR SEQ ID NO:12:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: Genomic DNA (xi) SEQUENCE DESCRIPTION: SEQ ID NO:12:

CTATTCTGCG TCTTCTGCTA AAAG                                                24

GLYCYL TRNA SYNTHETASE FROM *STREPTOCOCCUS PNEUMONIAE*

RELATED APPLICATIONS

This is a divisional of application Ser. No. 08/844,085 filed Apr. 18, 1997 now U.S. Pat. No. 5,756,330 which application claims benefit of UK application number 9608002.3, filed Apr. 18. 1996.

FIELD OF THE INVENTION

This invention relates to newly identified polynucleotides and polypeptides, and their production and uses, as well as their variants, agonists and antagonists, and their uses. In particular, in these and in other regards, the invention relates to novel polynucleotides and polypeptides of the glycyl tRNA synthetase (beta sub-unit) family, hereinafter referred to as "glyS (beta)," and the glycyl tRNA synthetase (alpha sub-unit) family, hereinafter referred to as "glyS (alpha)".

BACKGROUND OF THE INVENTION

The Streptococci make up a medically important genera of microbes known to cause several types of disease in humans, including, for example, otitis media, conjunctivitis, pneumonia, bacteremia, meningitis, sinusitis, pleural empyema and endocarditis, and most particularly meningitis, such as for example infection of cerebrospinal fluid. Since its isolation more than 100 years ago, *Streptococcus pneumoniae* has been one of the more intensively studied microbes. For example, much of our early understanding that DNA is, in fact, the genetic material was predicated on the work of Griffith and of Avery, Macleod and McCarty using this microbe. Despite the vast amount of research with *S. pneumoniae*, many questions concerning the virulence of this microbe remain. It is particularly preferred to employ Streptococcal genes and gene products as targets for the development of antibiotics.

The frequency of *Streptococcus pneumoniae* infections has risen dramatically in the past 20 years. This has been attributed to the emergence of multiply antibiotic resistant strains and an increasing population of people with weakened immune systems. It is no longer uncommon to isolate *Streptococcus pneumoniae* strains which are resistant to some or all of the standard antibiotics. This has created a demand for both new anti-microbial agents and diagnostic tests for this organism.

The t-RNA synthetases have a primary role in protein synthesis according to the following scheme:

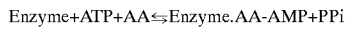

in which AA is an amino acid.

Inhibition of this process leads to a reduction in the levels of charged t-RNA and this triggers a cascade of responses known as the stringent response, the result of which is the induction of a state of dormancy in the organism. As such selective inhibitors of bacterial tRNA synthetase have potential as antibacterial agents. One example of such is mupirocin which is a selective inhibitor of isoleucyl t-RNA synthetase. Other t-RNA synthetases are now being examined as possible anti-bacterial targets, this process being greatly assisted by the isolation of the synthetase.

Clearly, there is a need for factors, such as the novel compounds of the invention, that have a present benefit of being useful to screen compounds for antibiotic activity. Such factors are also useful to determine their role in pathogenesis of infection, dysfunction and disease. There is also a need for identification and characterization of such factors and their antagonists and agonists which can play a role in preventing, ameliorating or correcting infections, dysfunctions or diseases.

The polypeptides of the invention have amino acid sequence homology to a known *Bacillus subtilis* glycyl tRNA synthetase beta sub-unit protein and *Bacillus subtilis* glycyl tRNA synthetase (alpha sub-unit) protein.

SUMMARY OF THE INVENTION

It is an object of the invention to provide polypeptides that have been identified as novel glyS (beta) and glyS (alpha) polypeptides by homology between the amino acid sequence set out in Table 1 [SEQ ID NO:2, 6 respectively] and a known amino acid sequence or sequences of other proteins such as *Bacillus subtilis* glycyl tRNA synthetase alpha or beta sub-unit protein.

It is a further object of the invention to provide polynucleotides that encode glyS (beta) or glyS (alpha) polypeptides, particularly polynucleotides that encode the polypeptide herein designated glyS (beta) and glyS (alpha).

In a particularly preferred embodiment of the invention the polynucleotide comprises a region encoding glyS (beta) polypeptides comprising the sequence set out in Table 1 [SEQ ID NO:1, 5] which includes a full length gene, or a variant thereof.

In another particularly preferred embodiment of the invention there is a novel glyS (beta) protein from *Streptococcus pneumoniae* comprising the amino acid sequence of Table 1 [SEQ ID NO:2], or a variant thereof.

In another particularly preferred embodiment of the invention there is a novel glyS (alpha) protein from *Streptococcus pneumoniae* comprising the amino acid sequence of Table 1 [SEQ ID NO:6], or a variant thereof.

In accordance with another aspect of the invention there is provided an isolated nucleic acid molecule encoding a mature, full length glyS (alpha) and glyS (beta) polypeptide expressible by the *Streptococcus pneumoniae* 0100993 strain contained in the deposited strain.

A further aspect of the invention there are provided isolated nucleic acid molecules encoding glyS (beta) and/or glyS (alpha), particularly *Streptococcus pneumoniae* glyS (alpha) and/or glyS (beta), including mRNAs, cDNAs, genomic DNAs. Further embodiments of the invention include biologically, diagnostically, prophylactically, clinically or therapeutically useful variants thereof, and compositions comprising the same.

In accordance with another aspect of the invention, there is provided the use of a polynucleotide of the invention for therapeutic or prophylactic purposes, in particular genetic immunization. Among the particularly preferred embodiments of the invention are naturally occurring allelic variants of glyS (beta) and glyS (alpha) and polypeptides encoded thereby.

Another aspect of the invention there are provided novel polypeptides of *Streptococcus pneumoniae* referred to herein as glyS (beta) or glyS (alpha) as well as biologically, diagnostically, prophylactically, clinically or therapeutically useful variants of either polypeptide, and compositions comprising the same.

Among the particularly preferred embodiments of the invention are variants of glyS (beta) or glyS (alpha) polypeptide encoded by naturally occurring alleles of the glyS (beta) or glyS (alpha) gene, respectively.

In a preferred embodiment of the invention there are provided methods for producing the aforementioned glyS (beta) and glyS (alpha) polypeptides.

In accordance with yet another aspect of the invention, there are provided inhibitors to such polypeptides, useful as antibacterial agents, including, for example, antibodies.

In accordance with certain preferred embodiments of the invention, there are provided products, compositions and methods for assessing glyS (beta) and/or glyS (alpha) expression, treating disease, for example, otitis media, conjunctivitis, pneumonia, bacteremia, meningitis, sinusitis, pleural empyema and endocarditis, and most particularly meningitis, such as for example infection of cerebrospinal fluid, assaying genetic variation, and administering a glyS (beta) polypeptide or polynucleotide to an organism to raise an immunological response against a bacteria, especially a *Streptococcus pneumoniae* bacteria In accordance with certain preferred embodiments of this and other aspects of the invention there are provided polynucleotides that hybridize to glyS (beta) and/or glyS (alpha) polynucleotide sequences, particularly under stringent conditions.

In certain preferred embodiments of the invention there are provided antibodies against glyS (beta) and/or glyS (alpha) polypeptides.

In other embodiments of the invention there are provided methods for identifying compounds which bind to or otherwise interact with and inhibit or activate an activity of a polypeptide or polynucleotide of the invention comprising: contacting a polypeptide or polynucleotide of the invention with a compound to be screened under conditions to permit binding to or other interaction between the compound and the polypeptide or polynucleotide to assess the binding to or other interaction with the compound, such binding or interaction being associated with a second component capable of providing a detectable signal in response to the binding or interaction of the polypeptide or polynucleotide with the compound; and determining whether the compound binds to or otherwise interacts with and activates or inhibits an activity of the polypeptide or polynucleotide by detecting the presence or absence of a signal generated from the binding or interaction of the compound with the polypeptide or polynucleotide.

In accordance with yet another aspect of the invention, there are provided glyS (beta) and/or glyS (alpha) agonists and antagonists, preferably bacteriostatic or bacteriocidal agonists and antagonists.

In a further aspect of the invention there are provided compositions comprising a glyS (beta) polynucleotide or a glyS (beta) polypeptide for administration to a cell or to a multicellular organism.

In a further aspect of the invention there are provided compositions comprising a glyS (alpha) polynucleotide or a glyS (alpha) polypeptide for administration to a cell or to a multicellular organism.

Various changes and modifications within the spirit and scope of the disclosed invention will become readily apparent to those skilled in the art from reading the following descriptions and from reading the other parts of the present disclosure.

GLOSSARY

The following definitions are provided to facilitate understanding of certain terms used frequently herein.

"Host cell" is a cell which has been transformed or transfected, or is capable of transformation or transfection by an exogenous polynucleotide sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A.M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M. Stockton Press, New York, 1991; and Carillo, H., and Lipman, D., SIAM *J. Applied Math.*, 48:1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1):387 (1984)), BLASTP, BLASTN, and FASTA (Atschul, S. F. et al., *J. Molec. Biol.* 215:403–410 (1990). The BLAST X program is publicly available from NCBI and other sources (*BLAST Manual*, Altschul, S., et al., NCBI NLM NIH Bethesda, Md. 20894; Altschul, S., et al.,*J. Mol. Biol.* 215:403–410 (1990). As an illustration, by a polynucleotide having a nucleotide sequence having, at least, for example, 95% "identity" to a reference nucleotide sequence of SEQ ID NO:1 it is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence. Analogously by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein.

"Polynucleotide(s)" generally refers to any polyribonucleotide or polydeoxribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins, and further includes homo- and hethero-dimers, trimers and tetramers of glyS (beta) and/or glyS (alpha). Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES,* 2nd Ed., T. E. Creighton, W. H. Freeman and Company, New York (1993) and Wold, F., Posttranslational Protein Modifications: Perspectives and Prospects, pgs. 1–12 in *POSTTRANSLATIONAL COVALENT MODIFICATION OF PROTEINS,* B. C. Johnson, Ed., Academic Press, New York (1983); Seifter et al., *Meth. Enzymol.* 182:626–646 (1990) and Rattan et al., *Protein Synthesis: Posttranslational Modifications and Aging,* Ann. N.Y. Acad. Sci. 663:48–62 (1992). Polypeptides may be branched or cyclic, with or without branching Cyclic, branched and branched circular polypeptides may result from post-translational natural processes and may be made by entirely synthetic methods, as well.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

DESCRIPTION OF THE INVENTION

The invention relates to novel glyS (beta) and glyS (alpha) polypeptides and polynucleotides as described in greater detail below. In particular, the invention relates to polypeptides and polynucleotides of a novel glyS (beta) and glyS (alpha) of *Streptococcus pneumoniae,* which is related by amino acid sequence homology to *Bacillus subtilis* glycyl tRNA synthetase beta or alpha sub-unit polypeptide, respectively. The invention relates especially to glyS (beta) comprising the nucleotide and amino acid sequences set out in Table 1 [SEQ ID NO:1] and Table 1 [SEQ ID NO:2] respectively, and to the glyS (beta) nucleotide sequences of the DNA in the deposited strain and amino acid sequences encoded thereby. The invention also relates especially to glyS (alpha) comprising the nucleotide and amino acid sequences set out in Table 1 [SEQ ID NO:5] and Table 1 [SEQ ID NO:6] respectively, and to the glyS (alpha) nucleotide sequences of the DNA in the deposited strain and amino acid sequences encoded thereby.

TABLE 1 glyS (beta) and glyS (alpha) Polynucleotide and Polypeptide Sequences (A) glyS (beta) sequences from *Streptococcus pneumoniae*
polynucleotide sequence [SEQ ID NO:1].

```
  5'-1 ATGACAAAAA ACTTATTAGT AGAACTCGGT CTTGAAGAAT TACCAGCCTA
    51 TGTTGTCACA CCAAGTGAAA AACAACTAGG CGAAAAAATG GCAGCCTTCC
   101 TCAAGGAAAA CCGCCTGTCT TTTGAAGCCA TTCAAACCTT CTCAACACCA
   151 CGTCGTTTGG CTGTTCGTGT GACTGGTTTA TCAGACAAAC AGTCTGATTT
   201 GACAGAAGAT TTCAAGGGAC CAGCAAAGAA AATTGCCTTG GATAGTGATG
   251 GAAACTTCAC CAAAGCAGCT CAAGGATTTG TCCGTGGAAA AGGCTTGACT
   301 GTTGAAGATA TCGAATTCCG TGAAATCAAG GGTGAAGAAT ATGTCTATGT
   351 CACTAAGGAA GAAGTTGGTC AAGCAGTTGA AGCCATTGTT CCTGGTGTTG
   401 TAGATGTCTT GAAGTCATTG ACTTTCCCTG TCAGCATGCA CTGGGCTGGA
   451 AACAGCTTTG AATACATCCG CCCTGTTCAC ACTTTAACTG TTCTCTTGGA
   501 TGAGCAAGAG TTTGACTTGG ATTTCCTTGA TATCAAGGGA GGTCGTGTGA
   551 GCCGTGGCCA TCGTTTTCTT GGGAAAGAAA CCAAAATTCA GTCAGCATTG
   601 AGCTATGAAG AAGACCTTCG TAAGCAGTTT GTAATCGCAG ATCCATGTGA
   651 ACGTGAGCAA ATGATTGTTG ACCAAATCAA GAAAATTGAG GCAAAACATG
   701 GTGTACGTAT CGAAATTGAT GCGGATTTGC TGAATGAAGT CTTGAATTTG
   751 GTTGAATACC CAACTGCCTT CATGGGAAGT TTTGATGCTA AATACCTTGA
   801 AGTTCCAGAA GAAGTCTTGG TAACTTCTAT GAAGGAACAC CAGCGTTACT
   851 TTGTTGTTCG TGATCAAGAT GGAAAACTCT TGCCAAACTT CATTTCTGTT
   901 CGTAACGGAA ACGCAGAGCG TTTGAAAAAT GTCATCAAAG GAAATGAAAA
   951 AGTCTTGGTA GCCCGCTTGG AAGACGGAGA ATTCTTCTGG CGTGAAGACC
  1001 AAAAATTGGT GATTTCAGAT CTTGTTGAAA AATTAAACAA TGTCACCTTC
  1051 CATGAGAAGA TTGGTTCCCT TCGTGAACAC ATGATTCGTA CGGGTCAAAT
  1101 CACTGTACTT TTGGCAGAAA AAGCTGGTTT GTCAGTGGAT GAAACAGTTG
  1151 ACCTTGCTCG TGCAGCAGCC ATTTACAAGT TTGACTTGTT GACAGGTATG
  1201 GTTGGTGAAT TGACGAACT  CCAAGGAATT ATGGGTGAAA AATACACCCT
  1251 TCTTGCTGGT GAAACTCCAG CGGTGGCAGC TGCTATTCGT GAACACTACA
  1301 TGCCTACATC AGCTGAAGGA GAACTTCCAG AGAGCAAGGT CGGTGCAGTT
  1351 CTAGCCATTG CAGACAAATT GGATACGATT TTGAGTTTCT TCTCAGTACG
  1401 ATTGATTCCA TCAGGTTCTA ATGACCCTTA TGCCCTTCGT CGTGCAACTC
  1451 AAGGTGTGGT TCGTATCTTG GATGCCTTTG GTTGGCACAT TGCTATGGAT
  1501 GAGCTGATTG ATAGCCTTTA TGCATTGAAA TTTGACAGTT TGACTTATGA
  1551 AAATAAAGCA GAGGTTATGG ACTTTATCAA GGCTCGTGTT GATAAGATGA
  1601 TGGGCTCTAC TCCAAAAGAT ATCAAGGAAG CAGTTCTTGC AGGTTCAAAC
  1651 TTTGTTGTGG CAGATATGTT GGAAGCAGCA AGTGCTCTCG TAGAAGTAAG
```

TABLE 1-continued glyS (beta) and glyS (alpha) Polynucleotide and Polypeptide Sequences

```
1701 CAAGGAAGAA GATTTTAAAC CATCTGTTGA ATCACTTTCT CGTGCCTTTA

1751 ACCTGGCTGA GAAGGCAGAA GGGGTTGCTA CAGTTGATTC AGCACTATTT

1801 GAGAATGACC AAGAAAAAGC TTTGGCAGAA GCAGTAGAAA CACTCGTTTT

1851 ATCAGGACCT GCAAGTCAGC AATTGAAACA ACTCTTTGCG CTTAGCCCAG

1901 TCATTGATGC TTTCTTTGAA ATACTATGG TAATGGCTGA AGATCAGGCT

1951 GTCCGTCAAA ATCGTTTGGC AATCTTGTCA CAACTAACCA AGAAAGCAGC

2001 TAAGTTTGCT TGTTTTAACC AAATTAACAC TAAATAA-3'
```

(B) glyS (beta) polypeptide sequence deduced from the polynucleotide sequence in this table [SEQ ID NO:2].

```
NH₂-1 MTKNLLVELG LEELPAYVVT PSEKQLGEKM AAFLKENRLS FEAIQTFSTP

51 RRLAVRVTGL SDKQSDLTED FKGPAKKIAL DSDGNFTKAA QGFVRGKGLT

101 VEDIEFREIK GEEYVYVTKE EVGQAVEAIV PGVVDVLKSL TFPVSMHWAG

151 NSFEYIRPVH TLTVLLDEQE FDLDFLDIKG GRVSRGHRFL GKETKIQSAL

201 SYEEDLRKQF VIADPCEREQ MIVDQIKKIE AKHGVRIEID ADLLNEVLNL

251 VEYPTAFMGS FDAKYLEVPE EVLUTSMKEH QRYFVVRDQD GKLLPNFISV

301 RNGNAERLKN VIKGNEKVLV ARLEDGEFFW REDQKLVISD LVEKLNNVTF

351 HEKIGSLREH MIRTGQITVL LAEKAGLSVD ETVDLARAAA IYDFDLLTGM

401 VGEFDELQGI MGEKYTLLAG ETPAVAAAIR EHYMPTSAEG ELPESKVGAV

451 LAIADKLDTI LSFFSVGLIP SGSNDPYALR RATQGVVRIL DAFGWHIAMD

501 ELIDSLYALK FDSLTYENKA EVMDFIKARV DKMMGSTPKD IKEAVLAGSN

551 FVVADMLEAA SALEVSKEE DFKPSVESLS RAFNLAEKAE GVATVDSALF

601 ENDQEKALAE AVETLVLSGP ASQQLKQLFA LSPVIDAFFE NTMVMAEDQA

651 VRQNRLAILS QLTKKAAKFA CFNQINTK-COOH
```

(C) glyS (beta) polynucleotide sequence embodiments [SEQ ID NO:1].

```
X-(R₁)ₙ-1 ATGACAAAAA ACTTATTAGT AGAACTCGGT CTTGAAGAAT TACCAGCCTA

51 TGTTGTCACA CCAAGTGAAA AACAACTAGG CGAAAAAATG GCAGCCTTCC

101 TCAAGGAAAA CCGCCTGTCT TTTGAAGCCA TTCAAACCTT CTCAACACCA

151 CGTCGTTTGG CTGTTCGTGT GACTGGTTTA TCAGACAAAC AGTCTGATTT

201 GACAGAAGAT TTCAAGGGAC CAGCAAAGAA AATTGCCTTG GATAGTGATG

251 GAAACTTCAC CAAAGCAGCT CAAGGATTTG TCCGTGGAAA AGGCTTGACT

301 GTTGAAGATA TCGAATTCCG TGAAATCAAG GGTGAAGAAT ATGTCTATGT

351 CACTAAGGAA GAAGTCATTG ACTTTCCCTG TCAGCATGCA CTGGGCTGGA

401 TAGATGTCTT GAAGTCATTG ACTTTCCCTG TCAGCATGCA CTGGGCTGGA

451 AACAGCTTTG AATACATCCG CCCTGTTCAC ACTTTAACTG TTCTCTTGGA

501 TGAGCAAGAG TTTGACTTGG ATTTCCTTGA TATCAAGGGA GGTCGTGTGA

551 GCCGTGGCCA TCGTTTTCTT GGGAAAGAAA CCAAAATTCA GTCAGCATTG

601 AGCTATGAAG AAGACCTTCG TAAGCAGTTT GTAATCGCAG ATCCATGTGA

651 ACGTGAGCAA ATGATTGTTG ACCAAATCAA GAAAATTGAG GCAAAACATG

701 GTGTACGTAT CGAAATTGAT GCGGATTTGC TGAATGAAGT CTTGAATTTG
```

TABLE 1-continued glyS (beta) and glyS (alpha) Polynucleotide and Polypeptide Sequences

```
 751 GTTGAATACC CAACTGCCTT CATGGGAAGT TTTGATGCTA AATACCTTGA
 801 AGTTCCAGAA GAAGTCTTGG TAACTTCTAT GAAGGAACAC CAGCGTTACT
 851 TTGTTGTTCG TGATCAAGAT GGAAAACTCT TGCCAAACTT CATTTCTGTT
 901 CGTAACGGAA ACGCAGAGCG TTTGAAAAAT GTCATCAAAG GAAATGAAAA
 951 AGTCTTGGTA GCCCGCTTGG AAGACGGAGA ATTCTTCTGG CGTGAAGACC
1001 AAAAATTGGT GATTTCAGAT CTTGTTGAAA AATTAAACAA TGTCACCTTC
1051 CATGAGAAGA TTGGTTCCCT TCGTGAACAC ATGATTCGTA CGGGTCAAAT
1101 CACTGTACTT TTGGCAGAAA AAGCTGGTTT GTCAGTGGAT GAAACAGTTG
1151 ACCTTGCTCG TGCAGCAGCC ATTTACAAGT TTGACTTGTT GACAGGTATG
1201 GTTGGTGAAT TTGACGAACT CCAAGGAATT ATGGGTGAAA AATACACCCT
1251 TCTTGCTGGT GAAACTCCAG CGGTGGCAGC TGCTATTCGT GAACACTACA
1301 TGCCTACATC AGCTGAAGGA GAACTTCCAG AGAGCAAGGT CGGTGCAGTT
1351 CTAGCCATTG CAGACAAATT GGATACGATT TTGAGTTTCT TCTCAGTAGG
1401 ATTGATTCCA TCAGGTTCTA ATGACCCTTA TGCCCTTCGT CGTGCAACTC
1451 AAGGTGTGGT TCGTATCTTG GATGCCTTTG GTTGGCACAT TGCTATGGAT
1501 GAGCTGATTG ATAGCCTTTA TGCATTGAAA TTTGACAGTT TGACTTATGA
1551 AAATAAAGCA GAGGTTATGG ACTTTATCAA GGCTCGTGTT GATAAGATGA
1601 TGGGCTCTAC TCCAAAAGAT ATCAAGGAAG CAGTTCTTGC AGGTTCAAAC
1651 TTTGTTGTGG CAGATATGTT GGAAGCAGCA AGTGCTCTCG TAGAAGTAAG
1701 CAAGGAAGAA GATTTTAAAC CATCTGTTGA ATCACTTTCT CGTGCCTTTA
1751 ACCTGGCTGA GAAGGCAGAA GGGGTTGCTA CAGTTGATTC AGCACTATTT
1801 GAGAATGACC AAGAAAAAGC TTTGGCAGAA GCAGTAGAAA CACTCGTTTT
1851 ATCAGGACCT GCAAGTCAGC AATTGAAACA ACTCTTTGCG CTTAGCCCAG
1901 TCATTGATGC TTTCTTTGAA AATACTATGG TAATGGCTGA AGATCAGGCT
1951 GTCCGTCAAA ATCGTTTGGC AATCTTGTCA CAACTAACCA AGAAAGCAGC
2001 TAAGTTTGCT TGTTTTAACC AAATTAACAC TAAATAA-(R2)n-Y
```

(D) glyS (beta) polypeptide sequence embodiments [SEQ ID NO:2].

```
X-(R1)n-1  MTKNLLVELG LEELPAYVVT PSEKQLGEKM AAFLKENRLS FEAIQTFSTP
      51  RRLAVRVTGL SDKQSDLTED FKGPAKKIAL DSDGNFTKAA QGFVRGKGLT
     101  VEDIEFREIK GEEYVYVTKE EVGQAVEAIV PGVVDVLKSL TFPVSMHWAG
     151  NSFEYIRPVH TLTVLLDEQE FDLDFLDIKG GRVSRGHRFL GKETKIQSAL
     201  SYEEDLRKQF VIADPCEREQ MIVDQIKKIE AKHGVRIEID ADLLNEVLNL
     251  VEYPTAFMGS FDAKYLEVPE EVLVTSMKEH QRYFVVRDQD GKLLPNFISV
     301  RNGNAERLKN VIKGNEKVLV ARLEDGEFFW REDQKLVISD LVEKLNNVTF
     351  HEKIGSLREH MIRTGQITVL LAEKAGLSVD ETVDLARAAA IYKFDLLTGM
     401  VGEFDELQGI MGEKYTLLAG ETPAVAAAIR EHYMPTSAEG ELPESKVGAV
     451  LAIADKLDTI LSFFSVGLIP SGSNDPYALR RATQGVVRIL DAFGWHIAMD
     501  ELIDSLYALK FDSLTYENKA EVMDFIKARV DKMMGSTPKD IKEAVLAGSH
```

TABLE 1-continued glyS (beta) and glyS (alpha) Polynucleotide and Polypeptide Sequences

```
      551 FVVADMLEAA SALVEVSKEE DFKPSVESLS RAFNLAEKAE GVATVDSALF

601 ENDQEKALAE AVETLVLSGP ASQQLKQLFA LSPVIDAFFE NTMVMAEDQA

651 VRQNRLAILS QLTKKAAKFA CFNQINTK-(R₂)ₙ-Y
```

(E) Sequences from *Streptococcus pneumoniae* glyS (beta) polynucleotide ORF sequence [SEQ ID NO:3].

```
    5'-1 CATCGTTTCT TGGGGAAAGA AACCAAAATT CAGTCAGCAT TGAGCTATGA

51 AGAAGACCTT CGTAAGCAGT TTGTAATCGC ANATCCATGT GAACGTGAGC

101 AAATGATTGT TGACCAAATC AAGAAAATTG AGGCAAAACA TGGTGTACGT

151 ATCGAAATTG ATGCGGATTT GCTGAATGAA GTCTTGAATT TGGTTGAATA

201 CCCNACTGCC TTCATGGGAA GTTTTGATGC TAAATNCCTT GAAGTTCCAG

251 AAGAAGTCTT GGTAACTTCT ATGAAGGAAC ACCAGCGTTA CTTTGTTGTT

301 CGTGATCAAG ATGGAAAACT CTTGCCAAAC TTCATTTCTG TTCGTAACGG

351 AAACGCAGAG CGTTTGAAAA ATGTCTTCAA AGGAAATGAA-3'
```

(F) glyS (beta) polypeptide sequence deduced from the polynucleotide ORF sequence in this table [SEQ ID NO:4].

```
    NH₂-1 HRFLGKETKI QSALSYEEDL RKQFVIAXPC EREQMIVDQI KKIEAKHGVR

51 IEIDADLLNE VLNLVEYPTA FMGSFDAKXL EVPEEVLVTS MKEHQRYFVV

101 RDQDGKLLPN FISVRNGNAE RLKNVFKGNE-COOH
```

(G) glyS (alpha) sequences from *Streptococcus pneumoniae* glyS (alpha) polynucleotide sequence [SEQ ID NO:5].

```
    5'-1 ATGTCTAAGA AATTAACATT TCAAGAAATT ATTTTGACTT TGCAACAATT

51 TTGGAATGAC CAAGGTTGTA TGCTTATGCA GGCTTATGAT AATGAAAAAG

101 GTGCGGGAAC AATGAGTCCT TACACTTTCC TTCGTGCTAT CGGACCTGAG

151 CCATGGAATG CAGCTTATGT AGAGCCATCA CGTCGTCCTG CTGACGGTCG

201 TTATGGGGAA AACCCTAACC GTCTCTACCA ACACCACCAA TTCCAGGTGG

251 TCATGAAGCC TTCTCCATCA AATATCCAAG AACTTTACCT TGAGTCTTTG

301 GAAAAATTGG GAATCAATCC TTTGGAGCAC GATATTCGTT TTGTTGAGGA

351 CAACTGGGAA AACCCATCAA CTGGTTCAGC TGGTCTTGGT TGGGAAGTTT

401 GGCTTGACGG AATGGAAATC ACTCAGTTCA CTTATTTCCA ACAAGTCGGT

451 GGATTGGCAA CTGGCCCTGT GACTGCGGAA GTTACCTATG GTTTGGAGCG

501 CTTGGCTTCT TACATTCAAG AAGTAGACTC TGTCTATGAT ATCGAGTGGG

551 CTGATGGTGT AAAATACGGA GAAATCTTTA TCCAGCCTGA GTATGAGCAC

601 TCAAAATATT CATTTGAAAT TCGAACCAA GAAATGTTGC TTGAAAACTT

651 TGATAAGTTT GAAAAAGAAG CTGGTCGTGC ATTAAAAGAA GGCTTGGTAC

701 ACCCTGCCTA TGACTATGTT CTCAAATGTT CACATACCTT TAATCTGCTT

751 GACGCGCGTG GTGCCGTATC TGTAACAGAG CGTGCAGGCT ATATCGCTCG

801 TATCCGTAAC TTGGCCCGTG TTGTAGCCAA AACCTTTGTT GCAGAACGCA

851 AACGCCTAGG TTACCCACTT TTGGATGAAG AAACACGAGT TAAACTTTTA

901 GCAGAAGACG CAGAATAG-3'
```

TABLE 1-continued glyS (beta) and glyS (alpha) Polynucleotide and Polypeptide Sequences (H) glyS (alpha) polypeptide sequence deduced from the
polynucleotide sequence [SEQ ID NO:5] in this table [SEQ ID NO:6].

```
NH2-1 MSKKLTFQEI ILTLQQFWND QGCMLMQAYD NEKGAGTMSP YTFLRAIGPE

51 PWNAAYVEPS RRPADGRYGE NPNRLYQHHQ FQVVMKPSPS NIQELYLESL

101 EKLGINPLEH DIRFVEDNWE NPSTGSAGLG WEVWLDGMEI TQFTYFQQVG

151 GLATGPVTAE VTYGLERLAS YIQEVDSVYD IEWADGVKYG EIFIQPEYEH

201 SKYSFEISNQ EMLLENFDKF EKEAGRALKE GLVHPAYDYV LKCSHTFNLL

251 DARGAVSVTE RAGYIARIRN LARVVAKTFV AERKRLGYPL LDEETRVKLL

301 AEDAE-COOH
```

(I) glyS (alpha) polynucleotide sequence embodiments [SEQ ID NO:5].

```
X-(R1)n-1 ATGTCTAAGA AATTAACATT TCAAGAAATT ATTTTGACTT TGCAACAATT

51 TTGGAATGAC CAAGGTTGTA TGCTTATGCA GGCTTATGAT AATGAAAAAG

101 GTGCGGGAAC AATGAGTCCT TACACTTTCC TTCGTGCTAT CGGACCTGAG

151 CCATGGAATG CAGCTTATGT AGAGCCATCA CGTCGTCCTG CTGACGGTCG

201 TTATGGGGAA AACCCTAACC GTCTCTACCA ACACCACCAA TTCCAGGTGG

251 TCATGAAGCC TTCTCCATCA AATATCCAAG AACTTTACCT TGAGTCTTTG

301 GAAAAATTGG GAATCAATCC TTTGGAGCAC GATATTCGTT TTGTTGAGGA

351 CAACTGGGAA AACCCATCAA CTGGTTCAGC TGGTCTTGGT TGGGAAGTTT

401 GGCTTGACGG AATGGAAATC ACTCAGTTCA CTTATTTCCA ACAAGTCGGT

451 GGATTGGCAA CTGGCCCTGT GACTGCGGAA GTTACCTATG GTTTGGAGCG

501 CTTGGCTTCT TACATTCAAG AAGTAGACTC TGTCTATGAT ATCGAGTGGG

551 CTGATGGTGT AAAATACGGA GAAATCTTTA TCCAGCCTGA GTATGAGCAC

601 TCAAAATATT CATTTGAAAT TTCGAACCAA GAAATGTTGC TTGAAAACTT

651 TGATAAGTTT GAAAAAGAAG CTGGTCGTGC ATTAAAAGAA GGCTTGGTAC

701 ACCCTGCCTA TGACTATGTT CTCAAATGTT CACATACCTT TAATCTGCTT

751 GACGCGCGTG GTGCCGTATC TGTAACAGAG CGTGCAGGCT ATATCGCTCG

801 TATCCGTAAC TTGGCCCGTG TTGTAGCCAA AACCTTTGTT GCAGAACGCA

851 AACGCCTAGG TTACCCACTT TTGGATGAAG AAACACGAGT TAAACTTTTA

901 GCAGAAGACG CAGAATAG-(R2)n-Y
```

(J) glyS (alpha) polypeptide sequence embodiments [SEQ ID NO:6].

```
X-(R1)n-1 MSKKLTFQEI ILTLQQFWND QGCMLMQAYD NEKGAGTMSP YTFLRAIGPE

51 PWNAAYVEPS RRPADGRYGE NPNRLYQHHQ FQVVMKPSPS NIQELYLESL

101 EKLGINPLEH DIRFVEDNWE NPSTGSAGLG WEVWLDGMEI TQFTYFQQVG

151 GLATGPVTAE VTYGLERLAS YIQEVDSVYD IEWADGVKYG EIFIQPEYEH

201 SKYSFEISNQ EMLLENFDKF EKEAGRALKE GLVHPAYDYV LKCSHTFNLL

251 DARGAVSVTE RAGYIARIRN LARVVAKTFV AERKRLGYPL LDEETRVKLL

301 AEDAE-(R2)n-Y
```

TABLE 1-continued glyS (beta) and glyS (alpha) Polynucleotide and Polypeptide Sequences (K) Sequences from *Streptococcus pneumoniae* glyS
(alpha) polynucleotide ORF sequence [SEQ ID NO:7].

```
 5'-1 GGTCTTGGTT GGGAAGTTTG GCTTGACGGA ATGGAAATCA CTCAGTTCAC

51 TTATTTCCAA CAAGTCGGTG GATTGGCAAC TGGCCCTGTG ACTGCGGAAG

101 TTACCTATGG TTTGGAGCGC TTGGCTTCTT ACATTCAAGA AGTAGACTCT

151 GTCTATGATA TCGAGTGGGC TGATGGTGTA AAATACGGAG AAATCTTTAT

201 C-3'
```

(L) glyS (alpha) polypeptide sequence deduced from the polynucleotide ORF sequence in this table [SEQ ID NO:8].

```
 NH2-1 GLGWEVWLDG MEITQFTYFQ QVGGLATGPV TAEVTYGLER LASYIQEVDS

51 VYDIEWADGV KYGEIFI-COOH
```

Deposited Materials

A deposit containing a *Streptococcus pneumoniae* 0100993 strain has been deposit with the National Collections of Industrial and Marine Bacteria Ltd. (herein "NCIMB"), 23 St. Machar Drive, Aberdeen AB2 IRY, Scotland on Apr. 11, 1996 and assigned deposit number 40794. The deposit was described as *Streptococcus pneumoniae* 0100993 on deposit. On Apr. 17, 1996 a *Streptococcus pneumoniae* 0100993 DNA library in *E. coli* was similarly deposited with the NCIMB and assigned deposit number 40800. The *Streptococcus pneumoniae* strain deposit is referred to herein as "the deposited strain" or as "the DNA of the deposited strain."

The deposited strain contains both the full length glyS (beta) and glyS (alpha) genes. The sequence of the polynucleotides contained in the deposited strain, as well as the amino acid sequence of the polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The strain will be irrevocably and without restriction or condition released to the public upon the issuance of a patent. The deposited strain is provided merely as convenience to those of skill in the art and is not an admission that a deposit is required for enablement, such as that required under 35 U.S.C. §112.

A license may be required to make, use or sell the deposited strain, and compounds derived therefrom, and no such license is hereby granted.

Polypeptides

The polypeptides of the invention include the polypeptides of Table 1 [SEQ ID NO:2, 4, 6, 8] (in particular the mature polypeptide) as well as polypeptides and fragments, particularly those which have the biological activity of glyS (beta) and/or glyS (alpha), and also those which have at least 70% identity to a polypeptide of Table 1 [SEQ ID NOS:2, 4, 6, 8] or the relevant portion, preferably at least 80% identity to a polypeptide of Table 1 [SEQ ID NOS:2, 4 6, 8], and more preferably at least 90% similarity (more preferably at least 90% identity) to a polypeptide of Table 1 [SEQ ID NOS:2, 4, 6, 8] and still more preferably at least 95% similarity (still more preferably at least 95% identity) to a polypeptide of Table 1 [SEQ ID NOS:2, 4, 6, 8] and also include portions of such polypeptides with such portion of the polypeptide generally containing at least 30 amino acids and more preferably at least 50 amino acids.

The invention also includes polypeptides of the formula set forth in Table 1 (D and J) [SEQ ID NO:2, 6] wherein, at the amino terminus, X is hydrogen, and at the carboxyl terminus, Y is hydrogen or a metal, $R_1$ and $R_2$ is any amino acid residue, and n is an integer between 1 and 1000. Any stretch of amino acid residues denoted by either R group, where R is greater than 1, may be either a heteropolymer or a homopolymer, preferably a heteropolymer.

A fragment is a variant polypeptide having an amino acid sequence that entirely is the same as part but not all of the amino acid sequence of the aforementioned polypeptides. As with glyS (beta) and glyS (alpha) polypeptides fragments may be "free-standing," or comprised within a larger polypeptide of which they form a part or region, most preferably as a single continuous region, a single larger polypeptide.

Preferred fragments include, for example, truncation polypeptides having a portion of an amino acid sequence of Table 1 [SEQ ID NOS:2, 4, 6, 8], or of variants thereof, such as a continuous series of residues that includes the amino terminus, or a continuous series of residues that includes the carboxyl terminus. Degradation forms of the polypeptides of the invention in a host cell, particularly a *Streptococcus pneumoniae*, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments which are those fragments that mediate activities of glyS (beta) and/or glyS (alpha), including those with a similar activity or an improved activity, or with a decreased undesirable activity. Also included are those fragments that are antigenic or immunogenic in an animal, especially in a human. Particularly preferred are fragments comprising receptors or domains of enzymes that confer a function essential for viability of *Streptococcus pneumoniae* or the ability to initiate, or maintain cause disease in an individual, particularly a human.

Variants that are fragments of the polypeptides of the invention may be employed for producing the corresponding full-length polypeptide by peptide synthesis; therefore, these variants may be employed as intermediates for producing the full-length polypeptides of the invention.

Polynucleotides

Another aspect of the invention relates to isolated polynucleotides, including the full length gene, that encode the glyS (beta) or glyS (alpha) polypeptide having a deduced amino acid sequence of Table 1 [SEQ ID NOS:2, 4, 6, 8] and polynucleotides closely related thereto and variants thereof.

Using the information provided herein, such as a polynucleotide sequence set out in Table 1 [SEQ ID NOS:1, 3, 5, 7], a polynucleotide of the invention encoding glyS (beta) and/or glyS (alpha) polypeptide may be obtained using standard cloning and screening methods, such as those for cloning and sequencing chromosomal DNA fragments from bacteria using *Streptococcus pneumoniae* 0100993 cells as starting material, followed by obtaining a full length clone. For example, to obtain a polynucleotide sequence of the invention, such as a sequence given in Table 1 [SEQ ID NOS:1, 3, 5, 7], typically a library of clones of chromosomal DNA of *Streptococcus pneumoniae* 0100993 in *E. coli* or some other suitable host is probed with a radiolabeled oligonucleotide, preferably a 17-mer or longer, derived from a partial sequence. Clones carrying DNA identical to that of the probe can then be distinguished using stringent conditions. By sequencing the individual clones thus identified with sequencing primers designed from the original sequence it is then possible to extend the sequence in both directions to determine the full gene sequence. Conveniently, such sequencing is performed using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, New York (1989). (see in particular Screening By Hybridization 1.90 and Sequencing Denatured Double-Stranded DNA Templates 13.70). Illustrative of the invention, the polynucleotide set out in Table 1 [SEQ ID NO:1] was discovered in a DNA library derived from *Streptococcus pneumoniae* 0100993.

The DNA sequence set out in Table 1 [SEQ ID NOS:1, 5] contains an open reading frame encoding a protein having about the number of amino acid residues set forth in Table 1 [SEQ ID NOS:2, 6 respectively] with a deduced molecular weight that can be calculated using amino acid residue molecular weight values well known in the art. The start codon of the DNA of full length glyS (beta) in Table 1 is nucleotide number 1 and last codon that encodes an amino acid is number 2034, the stop codon being the next codon following this last codon encoding an amino acid. The start codon of the DNA of full length glyS (alpha) in Table 1 is nucleotide number 1 and last codon that encodes an amino acid is number 915, the stop codon being the next codon following this last codon encoding an amino acid.

glyS (beta) and glyS (alpha) of the invention is structurally related to other proteins of the glycyl tRNA synthetase (alpha and beta subunit) family, as shown by the results of sequencing the DNA encoding glyS (beta) and glyS (alpha) of the deposited strain. The glyS (beta) protein exhibits greatest homology to *Bacillus subtilis* glycyl tRNA synthetase beta sub-unit protein among known proteins. glyS (beta) of Table 1 [SEQ ID NO:2] has about 45% identity over its entire length and about 65% similarity over its entire length with the amino acid sequence of *Bacillus subtilis* glycyl tRNA synthetase beta sub-unit polypeptide. The glyS (alpha) protein exhibits greatest homology to *Bacillus subtilis* glycyl tRNA synthetase (alpha sub-unit) protein among known proteins. glyS (alpha) of Table 1 [SEQ ID NO:6] has about 71% identity over its entire length and about 83% similarity over its entire length with the amino acid sequence of *Bacillus subtilis* glycyl tRNA synthetase (alpha subunit) polypeptide.

The invention provides a polynucleotide sequence identical over its entire length to each full length coding sequence in Table 1 [SEQ ID NO:1, 5]. Also provided by the invention is the coding sequence for the mature polypeptide or a fragment thereof, by itself as well as the coding sequence for the mature polypeptide or a fragment in reading frame with other coding sequence, such as those encoding a leader or secretory sequence, a pre-, or pro- or prepro-protein sequence. The polynucleotide may also contain non-coding sequences, including for example, but not limited to non-coding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86:821–824 (1989), or an HA tag (Wilson et al, *Cell* 37:767 (1984). Polynucleotides of the invention also include, but are not limited to, polynucleotides comprising a structural gene and its naturally associated sequences that control gene expression.

A preferred embodiment of the invention is the polynucleotide of comprising nucleotide 1 to 2034 set forth in SEQ ID NO:1 of Table 1 which encodes the glyS (beta) polypeptide. A further preferred embodiment of the invention is the polynucleotide of comprising nucleotide 1 to 915 set forth in SEQ ID NO:5 of Table 1 which encodes the glyS (alpha) polypeptide.

The invention also includes polynucleotides of the formula set forth in Table 1 (C and I) [SEQ ID NO:1 and 5 respectively] wherein, at the 5' end of the molecule, X is hydrogen, and at the 3' end of the molecule, Y is hydrogen or a metal, $R_1$ and $R_2$ is any nucleic acid residue, and n is an integer between 1 and 1000. Any stretch of nucleic acid residues denoted by either R group, where R is greater than 1, may be either a heteropolymer or a homopolymer, preferably a heteropolymer.

The term "polynucleotide encoding a polypeptide" as used herein encompasses polynucleotides that include a sequence encoding a polypeptide of the invention, particularly a bacterial polypeptide and more particularly a polypeptide of the *Streptococcus pneumoniae* glyS (beta) or glyS (alpha) comprising the amino acid sequence set out in Table 1 [SEQ ID NO:2 and 6 respectively]. The term also encompasses polynucleotides that include a single continuous region or discontinuous regions encoding the polypeptide (for example, interrupted by integrated phage or an insertion sequence or editing) together with additional regions, that also may contain coding and/or non-coding sequences.

The invention further relates to variants of the polynucleotides described herein that encode for variants of the polypeptide having a deduced amino acid sequence of Table 1 [SEQ ID NO:2, 6]. Variants that are fragments of the polynucleotides of the invention may be used to synthesize full-length polynucleotides of the invention.

Further particularly preferred embodiments are polynucleotides encoding glyS (beta) and/or glyS (alpha)

variants, that have the amino acid sequence of glyS (beta) or glyS (alpha) polypeptide of Table 1 [SEQ ID NO:2 and 6 respectively] in which several, a few, 5 to 10, 1 to 5, 1 to 3, 2, 1 or no amino acid residues are substituted, deleted or added, in any combination. Especially preferred among these are silent substitutions, additions and deletions, that do not alter the properties and activities of glyS (beta) or glyS (alpha).

Further preferred embodiments of the invention are polynucleotides that are at least 70% identical over their entire length to a polynucleotide encoding glyS (beta) and/or glyS (alpha) polypeptide having an amino acid sequence set out in Table 1 [SEQ ID NOS:2, 4, 6, 8], and polynucleotides that are complementary to such polynucleotides. Alternatively, most highly preferred are polynucleotides that comprise a region that is at least 80% identical over its entire length to a polynucleotide encoding glyS (beta) and/or glyS (alpha) polypeptide of the deposited strain and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides that encode polypeptides that retain substantially the same biological function or activity as the mature polypeptide encoded by the DNA of Table 1 [SEQ ID NO:1, 5].

The invention further relates to polynucleotides that hybridize to the herein above-described sequences. In this regard, the invention especially relates to polynucleotides that hybridize under stringent conditions to the herein above-described polynucleotides. As herein used, the terms "stringent conditions" and "stringent hybridization conditions" mean hybridization will occur only if there is at least 95% and preferably at least 97% identity between the sequences. An example of stringent hybridization conditions is overnight incubation at 42° C. in a solution comprising: 50% formamide, 5× SSC (150 mM NaCl, 15 mM trisodium citrate), 50 mM sodium phosphate (pH7.6), 5× Denhardt's solution, 10% dextran sulfate, and 20 micrograms/ml denatured, sheared salmon sperm DNA, followed by washing the hybridization support in 0.1× SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein.

The invention also provides a polynucleotide consisting essentially of a polynucleotide sequence obtainable by screening an appropriate library containing the complete gene for a polynucleotide sequence set forth in SEQ ID NO:1 or SEQ ID NO:5 under stringent hybridization conditions with a probe having the sequence of said polynucleotide sequence set forth in SEQ ID NO:1 or SEQ ID NO:5 respectively or a fragment thereof; and isolating said DNA sequence. Fragments useful for obtaining such a polynucleotide include, for example, probes and primers described elsewhere herein.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding glyS (beta) and/or glyS (alpha) and to isolate cDNA and genomic clones of other genes that have a high sequence similarity to the glyS (beta) and/or glyS (alpha) gene. Such probes generally will comprise at least 15 bases. Preferably, such probes will have at least 30 bases and may have at least 50 bases. Particularly preferred probes will have at least 30 bases and will have 50 bases or less.

For example, the coding region of the glyS (beta) and/or glyS (alpha) gene may be isolated by screening using the DNA sequence provided in SEQ ID NO:1 or 5 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

The polynucleotides and polypeptides of the invention may be employed, for example, as research reagents and materials for discovery of treatments of and diagnostics for disease, particularly human disease, as further discussed herein relating to polynucleotide assays.

Polynucleotides of the invention that are oligonucleotides derived from the sequences of SEQ ID NOS:1 and/or 2 and/or 5 and/or 6 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that may encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

Vectors, Host Cells, Expression

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as streptococci, staphylococci, enterococci *E. coli,* streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

For secretion of the translated protein into the lumen of the endoplasmic reticulum, into he periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Diagnostic Assays

This invention is also related to the use of the glyS (beta) and/or glyS (alpha) polynucleotides of the invention for use as diagnostic reagents. Detection of glyS (beta) and/or glyS (alpha) in a eukaryote, particularly a mammal, and especially a human, will provide a diagnostic method for diagnosis of a disease. Eukaryotes (herein also "individual(s)"), particularly mammals, and especially humans, infected with an organism comprising the glyS (beta) and/or glyS (alpha) gene may be detected at the nucleic acid level by a variety of techniques.

Nucleic acids for diagnosis may be obtained from an infected individual's cells and tissues, such as bone, blood, muscle, cartilage, and skin. Genomic DNA may be used directly for detection or may be amplified enzymatically by using PCR or other amplification technique prior to analysis. RNA or cDNA may also be used in the same ways. Using amplification, characterization of the species and strain of prokaryote present in an individual, may be made by an analysis of the genotype of the prokaryote gene. Deletions and insertions can be detected by a change in size of the amplified product in comparison to the genotype of a reference sequence. Point mutations can be identified by hybridizing amplified DNA to labeled glyS (beta) and/or glyS (alpha) polynucleotide sequences. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g., Myers et al., *Science,* 230:1242 (1985). Sequence changes at specific locations also may be revealed by nuclease protection assays, such as RNase and S1 protection or a chemical cleavage method. See, e.g., Cotton et al., *Proc. Natl. Acad. Sci.,* USA, 85:4397–4401 (1985).

Cells carrying mutations or polymorphisms in the gene of the invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to a nucleic acid encoding glyS (beta) and/or glyS (alpha) can be used to identify and analyze mutations. Examples of representative primers are shown below in Table 2 [SEQ ID NOS:9–12].

TABLE 2

Primers for amplification of glyS (beta) glyS (alpha) polynucleotides

| SEQ ID NO | PRIMER SEQUENCE | |
|---|---|---|
| 9 | 5'-ATGACAAAAAACTTATTAGTAGAA-3' | glyS (beta) forward |
| 10 | 5'-TTATTTAAGTGTTAATTTGGTTAA-3' | glyS (beta) reverse |
| 11 | 5'-ATGTCTAAGAAATTAACATTTCAA-3' | glyS (alpha) forward |
| 12 | 5'-CTATTCTGCGTCTTCTGCTAAAAG-3' | glyS (alpha) reverse |

The invention further provides these primers with 1, 2, 3 or 4 nucleotides removed from the 5' and/or the 3' end. These primers may be used for, among other things, amplifying glyS (beta) and/or glyS (alpha) DNA isolated from a sample derived from an individual. The primers may be used to amplify the gene isolated from an infected individual such that the gene may then be subject to various techniques for elucidation of the DNA sequence. In this way, mutations in the DNA sequence may be detected and used to diagnose infection and to serotype and/or classify the infectious agent.

The invention further provides a process for diagnosing, disease, preferably bacterial infections, more preferably infections by *Streptococcus pneumoniae,* and most preferably otitis media, conjunctivitis, pneumonia, bacteremia, meningitis, sinusitis, pleural empyema and endocarditis, and most particularly meningitis, such as for example infection of cerebrospinal fluid, comprising determining from a sample derived from an individual a increased level of expression of polynucleotide comprising a sequence of Table 1 [SEQ ID NO:1 and/or 5]. Increased or decreased expression of glyS (beta) and/or glyS (alpha) polynucleotide can be measured using any on of the methods well known in the art for the quantation of polynucleotides, such as, for example, amplification, PCR, RT-PCR, RNase protection, Northern blotting and other hybridization methods.

In addition, a diagnostic assay in accordance with the invention for detecting over-expression of glyS (beta) and/or glyS (alpha) protein compared to normal control tissue samples may be used to detect the presence of an infection, for example. Assay techniques that can be used to determine levels of a glyS (beta) and/or glyS (alpha) protein, in a sample derived from a host are well-known to those of skill in the art. Such assay methods include radioimmunoassays, competitive-binding assays, Western Blot analysis and ELISA assays.

Antibodies

The polypeptides of the invention or variants thereof, or cells expressing them can be used as an immunogen to produce antibodies immunospecific for such polypeptides. "Antibodies" as used herein includes monoclonal and polyclonal antibodies, chimeric, single chain, simianized antibodies and humanized antibodies, as well as Fab fragments, including the products of an Fab immunolglobulin expression library.

Antibodies generated against the polypeptides of the invention can be obtained by administering the polypeptides or epitope-bearing fragments, analogues or cells to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., *Nature* 256:495–497 (1975); Kozbor et al., *Immunology Today* 4:72 (1983); Cole et al., pg. 77–96 in *MONOCLONAL ANTIBODIES AND CANCER THERAPY,* Alan R. Liss, Inc. (1985).

Techniques for the production of single chain antibodies (U.S. Pat. No. 4,946,778) can be adapted to produce single chain antibodies to polypeptides of this invention. Also, transgenic mice, or other organisms such as other mammals, may be used to express humanized antibodies.

Alternatively phage display technology may be utilized to select antibody genes with binding activities towards the polypeptide either from repertoires of PCR amplified v-genes of lymphocytes from humans screened for possessing anti-glyS (beta), anti-glyS alpha) or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

If two antigen binding domains are present each domain may be directed against a different epitope—termed 'bispecific' antibodies.

The above-described antibodies may be employed to isolate or to identify clones pressing the polypeptides to purify the polypeptides by affinity chromatography.

Thus, among others, antibodies against glyS (beta)- and/or glyS (alpha)-polypeptide may be employed to treat infections, particularly bacterial infections and especially otitis media, conjunctivitis, pneumonia, bacteremia, meningitis, sinusitis, pleural empyema and endocarditis, and most particularly meningitis, such as for example infection of cerebrospinal fluid.

Polypeptide variants include antigenically, epitopically or immunologically equivalent variants that form a particular aspect of this invention. The term "antigenically equivalent derivative" as used herein encompasses a polypeptide or its equivalent which will be specifically recognized by certain antibodies which, when raised to the protein or polypeptide according to the invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably, the antibody or variant thereof is modified to make it less immunogenic in the individual. For example, if the individual is human the antibody may most preferably be "humanized"; where the complimentarity determining region(s) of the hybridoma-derived antibody has been transplanted into a human monoclonal antibody, for example as described in Jones, P. et al. (1986), Nature 321, 522–525 or Tempest et al., (1991) Biotechnology 9, 266–273.

The use of a polynucleotide of the invention in genetic immunization will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., J Biol Chem. 1989:264,16985), coprecipitation of DNA with calcium phosphate (Benvenisty & Reshef, PNAS, 1986:83, 9551), encapsulation of DNA in various forms of liposomes (Kaneda et al., Science 1989:243,375), particle bombardment (Tang et al., Nature 1992, 356:152, Eisenbraun et al., DNA Cell Biol 1993, 12:791) and in vivo infection using cloned retroviral vectors (Seeger et al., PNAS 1984:81, 5849).

Antagonists and Agonists—Assays and Molecules

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al, *Current Protocols in Immunology* 1(2): Chapter 5 (1991).

The invention also provides a method of screening compounds to identify those which enhance (agonist) or block (antagonist) the action of glyS (beta) and/or glyS (alpha) polypeptides, including dimers of glyS (beta) and glyS (alpha), or polynucleotides, particularly those compounds that are bacteriostatic and/or bacteriocidal. The method of screening may involve high-throughput techniques. For example, to screen for agonists or antagonists, a synthetic reaction mix, a cellular compartment, such as a membrane, cell envelope or cell wall, or a preparation of any thereof, comprising glyS (beta) and/or glyS (alpha) polypeptide and a labeled substrate or ligand of such polypeptide is incubated in the absence or the presence of a candidate molecule that may be a glyS (beta) and/or glyS (alpha) agonist or antagonist. The ability of the candidate molecule to agonize or antagonize the glyS (beta) and/or glyS (alpha) polypeptide is reflected in decreased binding of the labeled ligand or decreased production of product from such substrate. Molecules that bind gratuitously, i.e., without inducing the effects of glyS (beta) and/or glyS (alpha) polypeptide are most likely to be good antagonists. Molecules that bind well and increase the rate of product production from substrate are agonists. Detection of the rate or level of production of product from substrate may be enhanced by using a reporter system. Reporter systems that may be useful in this regard include but are not limited to colorimetric labeled substrate converted into product, a reporter gene that is responsive to changes in glyS (beta) and/or glyS (alpha) polynucleotide or polypeptide activity, and binding assays known in the art.

Another example of an assay for glyS (beta) and/or glyS (alpha) antagonists is a competitive assay that combines glyS (beta) and/or glyS (alpha) and a potential antagonist with glyS (beta)- and/or glyS (alpha)-binding molecules, recombinant glyS (beta) and/or glyS (alpha) binding molecules, natural substrates or ligands, or substrate or ligand mimetics, under appropriate conditions for a competitive inhibition assay. glyS (beta) and glyS (alpha) can be labeled, such as by radioactivity or a colorimetric compound, such that the number of glyS (beta) and/or glyS (alpha) molecules bound to a binding molecule or converted to product can be determined accurately to assess the effectiveness of the potential antagonist.

Potential antagonists include small organic molecules, peptides, polypeptides and antibodies that bind to a polynucleotide or polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing glyS (beta)- and/or glyS (alpha)-induced activities, thereby preventing the action of glyS (beta) and/or glyS (alpha) by excluding glyS (beta) and/or glyS (alpha) from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56:560 (1991); *OLIGODEOXYNUCLEOTIDES AS ANTISENSE INHIBITORS OF GENE EXPRESSION*, CRC Press, Boca Raton, Fla. (1988), for a description of these molecules). Preferred potential antagonists include compounds related to and variants of glyS (beta) and/or glyS (alpha)

Each of the DNA sequences provided herein may be used in the discovery and development of antibacterial compounds. The encoded protein, upon expression, can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide or inhibitor of the invention to interfere with the initial physical interaction between a pathogen and mammalian host responsible for sequelae of infection. In particular the molecules of the invention may be used: in the prevention of adhesion of bacteria, in particular gram positive bacteria, to mammalian extracellular matrix proteins on in-dwelling devices or to extracellular matrix proteins in wounds; to block glyS (beta) and/or glyS (alpha) protein-mediated mammalian cell invasion by, for example, initiating phosphorylation of mammalian tyrosine kinases (Rosenshine et al., *Infect. Immun.* 60:2211 (1992); to block bacterial adhesion between mammalian extracellular matrix proteins and bacterial glyS (beta) and/or glyS (alpha) proteins that mediate tissue damage and; to block the normal progression of pathogenesis in infections initiated other than by the implantation of in-dwelling devices or by other surgical techniques.

The antagonists and agonists of the invention may be employed, for instance, to inhibit and treat otitis media, conjunctivitis, pneumonia, bacteremia, meningitis, sinusitis, pleural empyema and endocarditis, and most particularly meningitis, such as for example infection of cerebrospinal fluid.

Vaccines

Another aspect of the invention relates to a method for inducing an immunological response in an individual, particularly a mammal which comprises inoculating the individual with glyS (beta) and/or glyS (alpha), or a fragment or variant thereof, such as glyS (alpha)-glyS (beta) fusions, adequate to produce antibody and/or T cell immune response to protect said individual from infection, particularly bacterial infection and most particularly *Streptococcus pneumoniae* infection. Also provided are methods whereby such immunological response slows bacterial replication. Yet another aspect of the invention relates to a method of inducing immunological response in an individual which comprises delivering to such individual a nucleic acid vector to direct expression of glyS (beta) and/or glyS (alpha), or a fragment, fusion or a variant thereof, for expressing glyS (beta) and/or glyS (alpha), or a fragment, fusion or a variant thereof in vivo in order to induce an immunological response, such as, to produce antibody and/ or T cell immune response, including, for example, cytokine-producing T cells or cytotoxic T cells, to protect said individual from disease, whether that disease is already established within the individual or not. One way of administering the gene is by accelerating it into the desired cells as a coating on particles or otherwise. Such nucleic acid vector may comprise DNA, RNA, a modified nucleic acid, or a DNA/RNA hybrid.

A further aspect of the invention relates to an immunological composition which, when introduced into an individual capable or having induced within it an immunological response, induces an immunological response in such individual to a glyS (beta) and/or glyS (alpha) or protein coded from either, wherein the composition comprises a recombinant glyS (beta) and/or glyS (alpha) or protein coded from either comprising DNA which codes for and expresses an antigen of said glyS (beta) and/or glyS (alpha) or protein coded from either. The immunological response may be used therapeutically or prophylactically and may take the form of antibody immunity or cellular immunity such as that arising from CTL or CD4+ T cells.

A glyS (beta) or glyS (alpha) polypeptide or a fragment of either or fused fragments from both may be fused with co-protein which may not by itself produce antibodies, but is capable of stabilizing the first protein and producing a fused protein which will have immunogenic and protective properties. Thus fused recombinant protein, preferably further comprises an antigenic co-protein, such as lipoprotein D from *Hemophilus influenzae*, Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. Science 273:352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with *Streptococcus pneumoniae* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of bacterial infection, particularly *Streptococcus pneumoniae* infection, in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused, e.g., by mechanical, chemical or thermal damage or by implantation of indwelling devices, or wounds in the mucous membranes, such as the mouth, mammary glands, urethra or vagina.

The invention also includes a vaccine formulation which comprises an immunogenic recombinant protein of the invention together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation insotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain glyS (beta) and glyS (alpha) protein, it is to be understood that this covers fragments of the naturally occurring protein and similar proteins with additions, deletions or substitutions which do not substantially affect the immunogenic properties of the recombinant protein.

Compositions, Kits and Administration

The invention also relates to compositions comprising the polynucleotide or the polypeptides discussed above or their agonists or antagonists. The polypeptides of the invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially Streptococcus pneumoniae wound infections.

Many orthopaedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of The invention may be used to bathe an indwelling device immediately before insertion. The active agent will preferably be present at a concentration of 1 μg/ml to 10 mg/ml for bathing of wounds or indwelling devices.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Each reference disclosed herein is incorporated by reference herein in its entirety. Any patent application to which this application claims priority is also incorporated by reference herein in its entirety.

EXAMPLES

The examples below are carried out using standard techniques, which are well known and routine to those of skill in the art, except where otherwise described in detail. The examples are illustrative, but do not limit the invention.

Example 1

Strain Selection, Library Production and Sequencing

The polynucleotides having the DNA sequence given in SEQ ID NO:1 and 5 were obtained from a library of clones of chromosomal DNA of Streptococcus pneumoniae in E. coli. The sequencing data from two or more clones containing overlapping Streptococcus pneumoniae DNAs was used to construct the contiguous DNA sequence in SEQ ID NO:1 and 5. Libraries may be prepared by routine methods, for example: Methods 1 and 2 below.

Total cellular DNA is isolated from Streptococcus pneumoniae 0100993 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and E. coli infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, BshI2351), and such fragments are size-fractionated according to standard procedures. EcoRI linkers are ligated to the DNA and the fragments then ligated into the vector Lambda ZapII that have been cut with EcoRI, the library packaged by standard procedures, and E. coli infected with the packaged library. The library is amplified by standard procedures.

Example 2

GlyS (Beta) and Glys (Alpha) Characterization

The enzyme mediated incorporation of radiolabelled amino acid into tRNA may be measured by the aminoacylation method which measures amino acid-tRNA as trichloroacetic acid-precipitable radioactivity from radiolabelled amino acid in the presence of tRNA and ATP (Hughes J., Mellows G. and Soughton S., 1980, FEBS Letters, 122:322–324). Thus inhibitors of glycyl tRNA synthetase heterodimer can be detected by a reduction in the trichloroacetic acid precipitable radioactivity relative to the control. Alternatively the tRNA synthetase catalysed partial PPi/ATP exchange reaction which measures the formation of radiolabelled ATP from PPi can be used to detect glycyl tRNA synthetase heterodimer inhibitors (Calender R. & Berg P., 1966, Biochemistry, 5, 1681–1690).

---

What is claimed is:

1. An isolated polypeptide comprising an amino acid sequence selected from the group consisting of;
   (a) an amino acid sequence having at least 95% identity with the amino acid sequence set forth in SEQ ID NO:2;
   (b) an amino acid sequence having at least 95% identity with the amino acid sequence set forth in SEQ ID NO:4;
   (c) an amino acid sequence having at least 95% identity with the amino acid sequence set forth in SEQ ID NO:6; and
   (d) an amino acid sequence having at least 95% identity with the amino acid sequence set forth in SEQ ID NO 8.

2. The isolated polypeptide of claim 1, wherein the isolated polypeptide consists of the amino acid sequence selected from the group consisting of:
   (a) an amino acid sequence having at least 95% identity with the amino acid sequence set forth in SEQ ID NO:2;
   (b) an amino acid sequence having at least 95% identity with the amino acid sequence set forth in SEQ ID NO:4;
   (c) an amino acid sequence having at least 95% identity with the amino acid sequence set forth in SEQ ID NO:6; and,
   (d) an amino acid sequence having at least 95% identity with the amino acid sequence set forth in SEQ ID NO:8.

3. An isolated polypeptide comprising an amino acid sequence selected from the group consisting of:
   (a) an amino acid sequence having at least 97% identity with the amino acid sequence set forth in SEQ ID NO:2;
   (b) an amino acid sequence having at least 97% identity with the amino acid sequence set forth in SEQ ID NO:4;
   (c) an amino acid sequence having at least 97% identity with the amino acid sequence set forth in SEQ ID NO:6; and,
   (d) an amino acid sequence having at least 97% identity with the amino acid sequence set forth in SEQ ID NO:8.

4. The isolated polypeptide of claim 3, wherein the isolated polypeptide consists of the amino acid sequence selected from the group consisting of:
   (a) an amino acid sequence having at least 97% identity with the amino acid sequence set forth in SEQ ID NO:2;
   (b) an amino acid sequence having at least 97% identity with the amino acid sequence set forth in SEQ ID NO:4;
   (c) an amino acid sequence having at least 97% identity with the amino acid sequence set forth in SEQ ID NO:6; and,
   (d) an amino acid sequence having at least 97% identity with the amino acid sequence, set forth in SEQ ID NO:8.

5. An isolated polypeptide comprising the amino acid sequence selected from the group consisting of:
   (a) an amino acid sequence as set forth in SEQ ID NO:2;
   (b) an amino acid sequence as set forth in SEQ ID NO:4;
   (c) an amino acid sequence as set forth in SEQ ID NO:6; and,
   (d) an amino acid sequence as set forth in SEQ ID NO:8.

6. The isolated polypeptide of claim 5, wherein the isolated polypeptide comprises the amino acid of (a).

7. The isolated polypeptide of claim 5, wherein the isolated polypeptide comprises the amino acid of (b).

8. The isolated polypeptide of claim 5, wherein the isolated polypeptide comprises the amino acid of (c).

9. The isolated polypeptide of claim 5, wherein the isolated polypeptide comprises the amino acid of (d).

10. An isolated polypeptide consisting of an amino acid sequence selected from the group consisting of:
   (a) an amino acid sequence as set forth in SEQ ID NO:2;
   (b) an amino acid sequence as set forth in SEQ ID NO:4;
   (c) an amino acid sequence as set forth in SEQ ID NO:6; and
   (d) an amino acid sequence as set forth in SEQ ID NO:8.

11. The isolated polypeptide of claim 10, wherein the isolated polypeptide consists of the amino acid sequence of (a).

12. The isolated polypeptide of claim 10, wherein the isolated polypeptide consists of the amino acid sequence of (b).

13. The isolated polypeptide of claim 10, wherein the isolated polypeptide consists of the amino acid sequence of (c).

14. The isolated polypeptide of claim 10, wherein the isolated polypeptide consists of the amino acid sequence of (d).

15. An isolated polypeptide comprising a polypeptide sequence selected from the group consisting of:
   (a) a first sequence which is selected from the group consisting of SEQ ID NOS:2, 4, 6 and 8;
   (b) a second sequence comprising a portion of the first sequence containing at least 30 amino acids;
   (c) a third sequence comprising a portion of the first sequence containing at least 50 amino acids;
   (d) a fourth sequence which is identical to the first sequence except that the fourth sequence has one mutation relative to the first sequence, wherein the mutation is a substitution, deletion or insertion of one amino acid;
   (e) a fifth sequence which is identical to the first sequence except that the fifth sequence has 1–5 mutations relative to the first sequence, wherein each mutation is a substitution deletion or insertion of one amino acid; and,
   (f) a sixth sequence which is identical to the first sequence except that the sixth sequence has 5–10 mutations relative to the first sequence, wherein each mutation is a substitution, deletion or insertion of one amino acid;
   wherein the isolated polypeptide is effective to induce antibodies to a polypeptide having the sequence of one of SEQ ID NOS:2, 4, 6 and 8.

16. The isolated polypeptide of claim 15, wherein the polypeptide sequence comprises the second sequence comprising a portion of the first sequence containing at least 30 amino acids.

17. The isolated polypeptide of claim 15, wherein the polypeptide sequence comprises the third sequence comprising a portion of the first sequence containing at least 50 amino acids.

18. The isolated polypeptide of claim 15, wherein the polypeptide sequence comprises the fourth sequence which is identical to the first sequence except that the fourth sequence has one mutation relative to the first sequence, wherein the mutation is a substitution, deletion or insertion of one amino acid.

19. The isolated polypeptide of claim 15, wherein the polypeptide sequence comprises the fifth sequence which is identical to the first sequence except that the fifth sequence has 1–5 mutations relative to the first sequence, wherein each mutation is a substitution, deletion or insertion of one amino acid.

20. The isolated polypeptide of claim 15, wherein the polypeptide sequence comprises the sixth sequence which is identical to the first sequence except that the sixth sequence has 5–10 mutations relative to the first sequence, wherein each mutation is a substitution, deletion or insertion of one amino acid.

21. The isolated polypeptide of claim 15, which is encoded by a polynucleotide comprising a nucleotide sequence selected from the group consisting of
   (a) a nucleotide sequence consisting of nucleotides 1 to 2034 as set forth in SEQ ID NO:1;
   (b) a nucleotide sequence as set forth in SEQ ID NO:3;
   (c) a nucleotide sequence consisting of nucleotides 1 to 915 as set forth in SEQ ID NO:5; and,
   (d) a nucleotide sequence as set forth in SEQ ID NO:7.

22. An isolated polypeptide encoded by an isolated first polynucleotide wherein the isolated first polynucleotide hybridizes under stringent conditions to a second polynucleotide which encodes the mature polypeptide of SEQ ID NOS:2, 4, 6 or 8, wherein stringent conditions comprise overnight incubation at 42° C. in a solution comprising: 50% formamide, 5× SSC (150 mM NacL, 15 mM trisodium citrate), 50 mM sodium phosphate (pH7.6), 5> Denhardt's solution, 10% dextran sulfate, and 20 micrograms/ml denatured, sheared salmon sperm DNA, followed by washing the filters in 0.1× SSC at about 65° C.; wherein the isolated polypeptide is tRNA synthetase polypeptide expressed by the DNA contained in NCIMB Deposit No. 40794.

23. An isolated polypeptide encoded by an isolated first polynucleotide wherein the isolated first polynucleotide hybridizes under stringent conditions to a reference polynucleotide consisting of a nucleotide sequence selected from the group consisting of
   (a) a nucleotide sequence consisting of nucleotides 1 to 2034 as set forth in SEQ ID NO:1;
   (b) a nucleotide sequence as set forth in SEQ ID NO:3;
   (c) a nucleotide sequence consisting of nucleotides 1 to 915 as set forth in SEQ ID NO:5; and,
   (d) a nucleotide sequence as set forth in SEQ ID NO:7;
   wherein stringent conditions comprise overnight incubation at 42° C. in a solution comprising: 50% formamide, 5× SSC (150 mM NacL, 15 mM trisodium citrate), 50 mM sodium phosphate (pH7.6), 5× Denhardt's solution, 10% dextran sulfate, and 20 micrograms/ml denatured, sheared salmon sperm DNA, followed by washing the filters in 0.1× SSC at about 65° C., wherein the isolated polypeptide comprises a sequence of at least 30 amino acids.

24. An isolated polypeptide comprising a polypeptide sequence selected from the group consisting of:
   (a) a first sequence which is selected from the group consisting of SEQ ID NOS:2, 4, 6 and 8;

(b) a second sequence comprising a portion of the first sequence containing at least 30 amino acids;
(c) a third sequence comprising a portion of the first sequence containing at least 50 amino acids;
(d) a fourth sequence which is identical to the first sequence except that the fourth sequence has one mutation relative to the first sequence, wherein each mutation is a substitution, deletion or insertion of one amino acid;
(e) a fifth sequence which is identical to the first sequence except that the fifth sequence has 1–5 mutations relative to the first sequence, wherein each mutation is a substitution deletion or insertion of one amino acid; and,
(f) a sixth sequence which is identical to the first sequence except that the sixth sequence has 5–10 mutations relative to the first sequence, wherein each mutation is a substitution, deletion or insertion of one amino acid,
wherein the isolated polypeptide is effective to induce antibodies to a polypeptide having the sequence of one of SEQ ID NOS:2, 4, 6 and 8, and wherein the isolated polypeptide has tRNA synthetase enzymatic activity.

25. The isolated polypeptide of claim 24, wherein the polypeptide sequence consists of the second sequence comprising a portion of the first sequence containing at least 30 amino acids.

26. The isolated polypeptide of claim 24, wherein the polypeptide sequence consists of the third sequence comprising a portion of the first sequence containing at least 50 amino acid.

27. The isolated polypeptide of claim 24, wherein the polypeptide sequence consists of the fourth sequence which is identical to the first sequence except that the fourth sequence has one mutation relative to the first sequence, wherein the mutation is a substitution, deletion or insertion of one amino acid.

28. The isolated polypeptide of claim 24, wherein the polypeptide sequence consists of the fifth sequence which is identical to the first sequence except that the fifth sequence has 1–5 mutations relative to the first sequence, wherein each mutation is a substitution, deletion or insertion of one amino acid.

29. The isolated polypeptide of claim 24, wherein the polypeptide sequence comprises the sixth sequence which is identical to the first sequence except that the sixth sequence has 5–10 mutations relative to the first sequence, wherein each mutation is a substitution, deletion or insertion of one amino acid.

* * * * *